United States Patent [19]

Edmundson et al.

[11] Patent Number: 5,279,830

[45] Date of Patent: Jan. 18, 1994

[54] MINERAL OIL FREE AND LANOLIN FREE COSMETIC COMPOSITION

[75] Inventors: Robert J. Edmundson, Germantown; Brian K. Mattox; Terry Jacks, both of Memphis, all of Tenn.

[73] Assignee: Intellectual Property Holding Co., Memphis, Tenn.

[21] Appl. No.: 773,663

[22] PCT Filed: Apr. 27, 1990

[86] PCT No.: PCT/US90/02211

§ 371 Date: Oct. 24, 1991

§ 102(e) Date: Oct. 24, 1991

[51] Int. Cl.$^5$ .................. A61K 31/74; A61K 7/021
[52] U.S. Cl. ........................ 424/401; 424/63; 424/64; 424/69
[58] Field of Search .............. 424/401, 63, 64, 69, 424/78.03; 514/844

[56] References Cited

U.S. PATENT DOCUMENTS

| | | | |
|---|---|---|---|
| 4,057,625 | 11/1977 | Hase | 514/772.5 |
| 4,066,789 | 1/1978 | Mores | 514/786 |
| 4,659,573 | 4/1987 | Frischling | 424/63 |
| 4,790,989 | 12/1988 | Hunter | 514/723 |
| 4,857,307 | 8/1989 | Suss | 424/69 |
| 4,868,220 | 9/1989 | Scheuffgen | 514/785 |

Primary Examiner—Thurman K. Page
Assistant Examiner—Sally Gardner
Attorney, Agent, or Firm—Sherman and Shalloway

[57] ABSTRACT

A cosmetic composition free of mineral oil and free of lanolin includes effective amounts of the following cosmetically acceptable ingredients (components): (A) at least one wax; (B) at least one triglyceride; (C) a mixture of esters including (i) a mixture of esters with a first mixture (i) having a maximum acid value 0.5 and a saponification value of 268–288; and a second mixture (ii) having a maximum acid value of 0.5 and a saponification value of 206–226; (D) distarch phosphate; (E) at least one bulking agent; (F) at least one colorant; and (G) optionally, at least one preservative. The composition is preferably formed into a cosmetic stick shape.

6 Claims, No Drawings

MINERAL OIL FREE AND LANOLIN FREE COSMETIC COMPOSITION

BACKGROUND

This invention relates to cosmetic cover compositions which are mineral oil free and lanolin free—i.e., contain no mineral oil and no lanolin (wool fat).

U.S. Pat. No. 4,659,573 issued to Frischling et al. on Apr. 21, 1987 discloses an ester blend comprising tridecyl trimellitate blended with at least one additional ester selected from the group consisting of dipentaerythritol hexacaprylate/hexacaprate, tridecyl stearate and neopentyl glycol dicaprylate/dicarprate. It is disclosed that the blend contains about 5 to about 85 wt. % tridecyl trimellitate based on the weight of the blend. It is also disclosed that these ester blends are a substitute for mineral oil in toiletry and cosmetics. According to U.S. Pat. No. 4,659,573 the disclosed ester blends are suitable for use in night creams, moisturizers, lotions, make-ups, face creams, day creams, body lotions, lipsticks and lip glosses.

The technical information brochure for SOFTISAN®649 (Hüls Troisdorf AG) discloses that this product is the glycerin ester of natural vegetable fatty acids, of an isostearic acid, and of the adipic acid, and that this product has the CTFA adopted name; caprylic/capric/isostearic/adipic triglyceride. It is disclosed that when SOFTISAN 649 is stirred in warm water it will form an emulsion having the properties of woolwax. It is also disclosed that emulsions containing SOFTISAN 649 have a better heat stability than emulsions with natural woolwax, they have a softer consistency, a good adhesion and leave a pleasant feeling on the skin. According to this brochure, SOFTISAN 649 is particularly suitable for skin care products, baby creams, sticks and other decorative cosmetics. The brochure gives formulations of several products containing SOFTISAN 649, amongst which there is included a sports cream stick on page 5.

Cosmetic cover compositions containing mineral oil and lanolin are known, and such compositions may not be ideally suitable for consumers who have oily skin and/or are sensitive to lanolin. These consumers would benefit from a composition that was free of mineral oil and free of lanolin, and they would further benefit if such a composition could also absorb some excess oil from the user's skin. Thus, a cosmetic cover composition free of mineral oil and free of lanolin, which could also absorb some excess oil from the user's skin, would be a welcome contribution to the art. Such a contribution is provided by this invention.

SUMMARY OF THE INVENTION

This invention provides a cosmetic composition, useful as a cover composition, which is free of mineral oil and free of lanolin. These compositions contain certain esters which can completely replace mineral oil in cosmetic cover compositions. Suitable esters useful as a mineral oil substitute are those which have mineral oil-like properties—i.e., suitable esters impart to the composition or provide the composition with characteristics which are the same as or similar to those characteristics which would have been imparted to or provided by mineral oil if the mineral oil had been present in the composition.

The compositions of this invention are also free of lanolin. These compositions contain trigylceride (glyceryl esters of fatty acids) which can completely replace lanolin in cosmetic compositions. Suitable triglycerides useful as a lanolin substitute are those triglycerides which have lanolin-like properties—i.e., suitable triglycerides impart to the composition or provide the composition with characteristics which are the same as or similar to those characteristics which would have been imparted to or provided by lanolin if the lanolin had been present in the composition.

The compositions of this invention also contain distarch phosphate which, without wishing to be bound by theory, is believed to function as an absorber of oil from the skin of the user.

The compositions of this invention also contain at least one wax, triglyceride, bulking agent, colorant, and optionally, preservative. The term "at least one" as used herein means one, more than one, or a mixture.

The term "suitable for use in cosmetic compositions", as used herein, means cosmetically acceptable and refers to those materials known in the art as being useable in cosmetic compositions, such as those materials disclosed in Nikitakis, J. M., editor, *CTFA Cosmetic Ingredient Handbook*, First Edition, copyright 1988, published by The cosmetic, Toiletry and Fragrance Association, Inc., 1110 Vermont Avenue, N.W., Washington, D.C., 20005, the disclosure of which is incorporated herein by reference thereto, and which is hereinafter referred to as the "CTFA Handbook."

DETAILED DESCRIPTION OF THE INVENTION

This invention provides a cosmetic composition free of mineral oil and free of lanolin comprising:
- (A) an effective amount of at least one wax suitable for use in cosmetic compositions;
- (B) an effective amount of at least one triglyceride suitable for use in cosmetic compositions;
- (C) an effective amount of a mixture of esters suitable for use in cosmetic compositions, said mixture comprising:
  - (i) an effective amount of a mixture of esters with said mixture (i) having a maximum acid value of 0.5 and a saponification value of 268–288; and
  - (ii) an effective amount of a mixture of esters with said mixture (ii) having a maximum acid value of 0.5 and a saponification value of 206–266;
- (D) an effective amount of distarch phosphate;
- (E) an effective amount of at least one bulking agent suitable for use in cosmetic compositions;
- (F) an effective amount of at least one colorant suitable for use in cosmetic compositions; and
- (G) optionally, an effective amount of at least one preservative suitable for use in cosmetic compositions.

This invention also provides articles of manufacture comprising the compositions of this invention manufactured in a solid rigid form suitable for use as a cosmetic. Preferably the compositions are manufactured in the form or shape of a cover stick.

Although the compositions can be formed by known procedures into any suitable solid shape for the ultimate end product, preferably the composition is formed into a cosmetic stick shape—e.g., a cylindrical shape having a slanted tip such as a "lipstick shape." The shaped composition can then be placed in any suitable dispensing package such as a lipstick type container wherein the composition is advanced by, for example, turning the barrel of the dispensing package or container. Thus for example, the composition can be cylindrical in shape wherein the cylinder is about 6.3 to about 7.6 cm in length and preferably about 6.8 to about 7.1, the diameter is about 0.72 to about 0.77 cm with about 0.73 to about 0.75 being preferred, and the tip of the cylinder is formed so as to have an angle of about 43 to about 47 degrees and preferably about 44 to about 46 degrees.

The compositions of this invention contain an effective amount of at least one cosmetically acceptable wax. Waxes which may prove useful include those listed in the CTFA Handbook cited above and already incorporated herein by reference thereto. Thus, representative examples include ozokerite, ceresin, paraffin, candelilla, crnauba, and the like. Preferably the wax is selected from the group consisting of: ozokerite and ceresin. Most preferably ozokerite is used. Usually, the wax is present in amounts of about 10.0% to about 15% by weight of the total composition with about 13% to about 14% by weight being preferred.

The compositions of this invention also contain an effective amount of at least one cosmetically acceptable triglyceride. Triglyceride, as used herein, refers to the glyceryl esters of fatty acids and includes those esters which have been hydrogenated to reduce or eliminate unsaturation. Those skilled in the art will appreciate that the triglycerides are the chief constituent of fats and oils, and that the triglycerides have the general formula:

$$CH_2(OOCR_1)CH(OOCR_2)CH_2(OOCR_3)$$

wherein $R_1$, $R_2$ and $R_3$ are usually of different chain lengths, e.g., $C_1-C_{31}$ and more usually $C_2-C_{24}$. Fatty acids are well known in the art, see for example, *Biochemicals Organic Compounds for Research and Diagnostic Reagents*, Sigma Chemical Company, pp. 924-925, 1989, the disclosure of which is incorporated herein by reference thereto.

Thus, the triglycerides which are useable include those materials (substances) which are known to those skilled in the art as fats and oils. Suitable triglycerides which may prove useful include, those materials listed as fats and oils in the CTFA Handbook cited above and already incorporated herein by reference thereto. Preferably, triglycerides are used rather than a fat or oil containing triglycerides. Representative triglycerides include the glyceryl esters of caprylic acid, capric acid, isostearic acid (identified in the CTFA Handbook as a mixture of branched chain 18 carbon aliphatic acids), adipic acid, lauric acid and stearic acid.

The preferred fatty acids are selected from the group consisting of caprylic acid, isostearic acid and adipic acid. Preferably a mixture of the glyceryl esters of the above mentioned preferred fatty acids are used. The preferred ester mixture normally contains, by weight of the ester mixture, about 10 to about 14% glyceryl ester of caprylic acid, about 7.0 to about 11.0% glyceryl ester of capric acid, about 39.0 to about 41.0% glyceryl ester of isostearic acid, and about 17.0 to about 21.0% glyceryl ester of adipic.

The preferred triglyceride is caprylic/capric/isostearic/adipic triglyceride which is identified by the CTFA Handbook as the mixed ester of caprylic, capric, isostearic acids with a dimer of glycerin. Caprylic/capric/isostearic/adipic triglyceride is commercially available under the product designation SOFTISAN 649 from Hüls American, Inc., Rockleigh, N.J. SOFTISAN 649 is reported to contain: 12% caprylic acid, 9% capric acid, 19% adipic acid, 41% isostearic acid, and 10% 12-hydroxystearic acid with the remainder being a mixture of $C_6$, $C_{12}$, $C_{14}$ and $C_{16}$ fatty acids.

Other triglycerides which may prove suitable include: caprylic/capric/lauric triglyceride; caprylic/capric/linolaic triglyceride; caprylic/capric/stearic triglyceride; and caprylic/carpic triglyceride. These triglycerides are known in the art-see the CTFA Handbook for example.

Normally, the triglyceride is used in amounts of about 3 to about 10% by weight of the total composition with about 4 to about 5% by weight being preferred and about 5 to about 6% by weight being most preferred.

The compositions of this invention, as stated previously, contain no mineral oil. In place of the mineral oil there is used an effective amount of a mineral oil substitute. The mineral oil substitute provides the same or similar characteristics to the composition that mineral oil would have provided had the mineral oil been present. It is contemplated that one or more esters having mineral oil characteristics, or imparting mineral oil like characteristics to the composition, may be used.

An effective amount of a mixture of esters may be used as a mineral oil substitute in the compositions of this invention. Thus, an effective amount of a mixture of esters comprising:

(i) an effective amount of a mixture of esters with said mixture (i) having a maximum acid value of 0.5 and a saponificatioin value of 268-288; and (ii) an effective amount of a mixture of esters with said mixture (ii) having a maximum acid value of 0.5 and a saponification value of 206-266 may be used in the compositions of this invention.

The ratio of ester mixture (i) above to (ii) above is normally about 1.5 to about 1 with about 1 to about 1 being preferred. Thus, (i) and (ii) are each usually present in the amounts of about 15 to about 25% (about 30 to about 50% total of (i) plus (ii)) by weight of the total composition with about 17 to about 23% (about 34 to about 46% total of (i) plus (ii)) being preferred and about 18 to about 22% (about 36 to about 44% total of (i) plus (ii)) being most preferred and about 19 to about 21% (about 38 to about 42% total of (i) plus (ii)) being even more preferred.

Tridecyl trimellitate (TDTM) can be blended with at least one other ester, preferably at least two other esters, to formulate a blend which duplicates the viscosity and feel of mineral oil for use in cosmetics. The esters generally blended with TDTM will be lower in viscosity than TDTM. The preferred esters for blending with TDTM are tridecyl stearate (TDS), Neopentylglycol dicaprylate/dicaprate (NPGC) and dipentaerythritol hexacaprylate/hexacaprate (DPHC). Particularly advantageous results are achieved when TDTM is blended with TDS, NPGC and DPHC. The selection and quantity of the esters which are blended with TDTM will vary depending on the desired viscosity of the final blend and the feel which the final blend is intended to have.

Illustrative, non-limiting examples of other esters which may be blended with TDTM are isodecyl trimellitate, isopropyl myristate, isopropyl palmitate, tridecyl myristate, tridecyl palmitate, isodecyl trimellitate, propylene glycol dicaprate/dicaprylate, neopentyl glycol dicaprate and trisodecyl trimellitate.

Depending on the desired viscosity and other properties desired, the amount of TDTM in a particular blend can vary from about 5 to about 85 wt %, based on the ester blend, preferably about 5 to about 60 wt %, more preferably about 8 to about 45 wt %, most preferably about 10 to about 38 wt %, e.g., about 12 to about 37 wt %. Where the ester blend is a low viscosity blend, e.g., 70 S.S.U. at 100° F., the TDTM is preferably utilized at about 10 to about 14 wt %. For an intermediate viscosity blend, e.g., 130 S.S.U. at 100° F., the TDTM is preferably utilized at about 33 to about 38 wt % based on the ester blend, and for a high viscosity blend, e.g., 350 S.S.U. at 100° F., the TDTM is preferably utilized at about 38 to about 42 wt %, based on the ester blend. The balance of the ester blend can be at least one additional ester, preferably at least two additional esters, each of the two esters being utilized at about 2 to about 60 wt % based on the ester blend depending on the particular properties desired. In a preferred blend where TDS is one of the two or more additional esters blended with the TDTM, it can be utilized at about 5 to about 55 wt %. Where the ester blend is a low viscosity blend, e.g., less than 150 S.S.U., the TDS is preferably utilized at about 40 to about 50 wt %, more preferably about 42 to about 46 wt %, based on the ester blend. Where the ester blend is a higher viscosity blend, the TDS is preferably utilized at about 5 to about 20 wt %, more preferably at about 5 to about 12 wt %, most preferably at about 6 to about 9 wt % based on the ester blend.

Where NPGC is one of the additional esters, it is preferably utilized at about 2 to about 55 wt % based on the ester blend. For lower viscosity blends, the NPGC is preferably utilized at about 40 to about 50 wt % based on the ester blend, more preferably about 42 to about 45 wt %. For higher viscosity blends, the NPGC is preferably utilized at about 2 to about 10 wt %, more preferably about 3 to about 5 wt %.

Where DPHC is one of the additional ester blends it can be utilized at about 10 to about 55 wt %. For lower viscosity blends the DPHC is preferably utilized at about 12 to about 25 wt % based on the ester blend, more preferably at about 16 to about 20 wt %, most preferably at about 17 to about 19 wt % based on the ester blend. For higher viscosity blends, the DPHC is preferably utilized at about 40 to about 55 wt % based on the ester blend, more preferably about 42 to about 52 wt. %, most preferably about 46 to about 50 wt %.

These blends are known in the art, for example, see U.S. Pat. No. 4,659,573 issued to Frischling et al. on Apr. 21, 1987, the disclosure of which is incorporated herein by reference thereto.

Generally, the ester mixture used in the compositions of this invention contains:

(A) Tridecyl stearate in amounts of about 9 to about 12% by wt of the total composition with about 9.0 to about 11.0% being preferred and about 10 to about 11% being most preferred;

(B) neopentylglycol dicaprylate/dicaprate in amounts of about 8 to about 11% by wt of the total composition with about 9 to about 11% being preferred and about 9 to about 10% being most preferred;

(C) tridecyl trimellitate in amounts of about 9 to about 12% by weight of the total composition with about 9 to about 11% being preferred and about 10 to about 11% being most preferred;

(D) dipentaerythrityl (dipentaerythritol) hexacaprylate/hexacaprate in amounts of about 8 to about 11.5% by weight of the composition with about 9 to about 11% being preferred and about 9 to about 10% being most preferred.

A mixture of esters having the maximum acid value (0.5) and saponification value (268-288) of (i) above is available commercially under the product designation LIPOVOL MOS-350 from LIPO CHEMICALS Inc, Patterson, N.J. LIPOVOL MOS-350 is reported to contain: (1) 47.55% by weight of dipentaerylthrityl hexaceparylate/hexacaprate; (2) 40.25% by weight of tridecyl trimellitate; (3) 8.80% by weight of tridecyl stearate; and (4) 3.40% by wt of neopentylglycol dicaprylate/dicaprate.

A mixture of esters having the maximum acid value (0.5) and saponification value (206-226) of (ii) above is available commercially under the product designation LIPOVOL MOS-70 from LIPO CHEMICALS INC., Patterson, N.J. LIPOVOL MOS-70 is reported to contain (i) 44.00% by wt tridecyl stearate; (2) 44.00% by wt neopentylglycol decaprylate/decaprate; and (3) 12.00% by wt tridecyl trimellitate.

Effective amounts of distarch phosphate are used in the compositions of this invention. Distarch phosphate, according to the CTFA Handbook, is the product produced by the cross-linking of starch with sodium metaphosphate. Distarch phosphate is commercially available from, for example, National Starch Co. In general, suitable amounts of distarch phosphate are within the range of about 2.5 to about 7.5% by weight of the total composition with about 3 to about 7% by weight being preferred and about 4 to about 6% by wt being most preferred and about 4.5 to about 5.5% being even more preferred.

Bulking agents suitable for use in cosmetics are also present in effective amounts in the composition of this invention. Suitable bulking agents which may prove useful include those bulking agents disclosed in the CTFA Handbook which has already been cited above and has already been incorporated herein by reference thereto. Thus, representative bulking agents include talc, kaolin, mica, zinc stearate, zinc oxide, and the like. Preferably, the bulking agent is selected from the group consisting of talc, kaolin, mica, and zinc oxide. Most preferably kaolin is used.

In general the total amount of bulking agent used is about 3 to about 6% by weight of the total composition with about 3 to about 4.5% by wt being preferred and about 3.0 to about 4.0% being most preferred.

Cosmetically acceptable colorants are also present in effective amounts in the compositions of this invention. Colorants which may prove useful include those colorants disclosed in the CTFA Handbook which, as stated previously, has already been cited herein and has already been incorporated herein by reference thereto. Representative colorants (coloring agents) may include: titantium dioxide; lomicron pink (a commercially available blend of iron oxides and talc); iron oxides such as yellow oxide, and black oxide; and the like. Preferably the colorants are selected from the group consisting of: titanium dioxide; lomicron pink; and the iron oxides known as yellow oxide and black oxide.

Generally, the colorant is present in amounts of about 28 to about 35% by weight of the total composition with about 29 to about 32% by wt being preferred and about 30 to about 32% by wt being most preferred. Preferably the composition contains about 27 to about 33% by weight of the composition of titanium dioxide with about 29 to about 30% by wt being preferred. It is preferred that, in addition to the titanium dioxide, the composition also contain: (a) lomicron pink in amounts of about 0.5 to about 1.00% by weight of the total composition with about 0.80 to about 1.00% by wt being preferred and about 0.80 to about 0.90% by wt being most preferred; (b) yellow oxide (an iron oxide) in amounts of about 0.50 to about 1.00% by weight of the total composition with about 0.80 to about 1.00% by wt being preferred and about 0.80 to about 0.90% by weight being most preferred; and (c) black oxide (an iron oxide) in amounts of about 0.01 to about 0.05% by weight of the total composition and about 0.02 to about 0.04% by wt being preferred.

The compositions of this invention optionally contain an effective amount of at least one preservative. Preferably the preservative is present. Preservatives which may prove useful include those preservatives disclosed in the CTFA Handbook which is already been cited above and which has already been incorporated herein by reference thereto. Examples of preservatives include: butylated hydroxyanisole, butyl paraben, propyl paraben, methyl paraben, and the like. Preferably the preservative is selected from the group consisting of butylated hydroxyanisole (e.g. such as that available under the product designation TENOX), butyl paraben, and propyl paraben. A suitable combination of preservatives for use is butylated hydroxyanisole, butyl paraben, and propyl paraben.

Generally, the preservative is present in an amount of about 0.20 to about 0.5% by weight of the total composition with about 0.20 to about 0.3% by wt being preferred and about 0.2 to about 0.25% by wt being most preferred. Preferably the composition contains: (1) butylated hydroxyanisole in an amount of about 0.02 to about 0.04% by weight of the total composition with about 0.025 to about 0.035% by wt being preferred and about 0.03% by wt being most preferred; (2) butyl paraben in an amount of about 0.05 to about 0.2% by weight of the total composition with about 0.05 to about 0.15% by wt preferred and about 0.1% by wt being most preferred; (3) propyl paraben in an amount of about 0.05 to about 0.2% by wt of the total composition with about 0.05 to about 0.15% by wt being preferred and about 0.1% by wt being most preferred.

The ingredients forming the compositions of this invention may be blended together in any suitable mixing device capable of adequately mixing the ingredients together at a suitable temperature of produce a uniform blend. Generally, the temperature needed to adequately blend the ingredients together is dependent upon the temperature needed to melt the particular wax being used. The temperature selected is high enough to melt the wax and allow uniform blending of ingredients but not so high as to cause undue degradation of the various ingredients used. Normally, a temperature within the range of about 70° to about 85° C. will suffice with about 80° to about 83° C. being preferred. The ingredients are blended together using sufficient shear to yield a uniform blend of ingredients in a reasonable amount of time. Normally mixing devices which can provide a shear rate of about 800 to about 1200 RPM, with about 850 to about 950 RPM being preferred, will be suitable. A reasonable amount of time will usually be about 30 to about 50 minutes with about 35 to about 45 minutes being preferred.

Although the order of blending ingredients is not critical, it is preferred to: (1) melt the wax; (2) then add the triglyceride and mineral-oil substitute (the mixture of esters having or imparting mineral-oil characteristics); (3) blend (1) and (2) together along with the preservatives; (4) blend the distarch phosphate with the resulting mixture of (3); (5) add the colorants and bulking agents, preferably as a premix, to the resulting mixture from (4) (note, the premix may have a preservative added to it to maintain its integrity until use); and (6) blend the resulting mixture from (5) together until uniform. During the blending steps a temperature is maintained that is high enough to prevent the wax from solidifying but not so high as to cause undue degradation of the ingredients. The resulting final mixture can be strained through a suitable material—e.g., cheese cloth—and stored in suitable containers.

The composition can be formed into suitable shapes, e.g., a stick shape similar to that of lipstick, by methods known in the art. For example, pouring the molten mass into metal molds.

The following examples are illustrative only and should not be construed as limiting the invention in any way. Those skilled in the art will appreciate that variations are possible which are within the spirit and scope of the appended claims.

EXAMPLE I

A composition of this invention was prepared from the ingredients given in Table I.

TABLE I

| Ingredient | % by wt |
| --- | --- |
| White ozokerite 170 MF | 13.030 |
| SOFTISAN 649 | 5.800 |
| LIPOVOL MOS 70 | 20.110 |
| LIPOVOL MOS 350 | 20.727 |
| Butylated hydroxyanisole | 0.030 |
| Butyl paraben | 0.100 |
| Distarch phosphate | 5.000 |
| Titanium dioxide | 28.209 |
| Kaolin | 2.942 |
| Lomicron Pink | 2.009 |
| Yellow Oxide | 1.878 |
| Black Oxide | 0.065 |
| Propyl paraben | 0.100 |

The ingredients in Table I were combined together using the following procedure. A sample portion (i.e., about 5.0%) of LIPOVOL MOS 70 was added to a steam jacketed kettle (A) equipped with an appropriate mixer and maintained at about 85° C. The white ozokerite (obtained from Strahl & Pitsch) was melted in this kettle.

Next the SOFTISAN 649, the remainder of the LIPOVOL MOS 70, and the LIPOVOL MOS 350 was added to another steam jacketed kettle (B) equipped with a high shear mixer. These ingredients were heated to about 80° C. to about 85° C. and mixed until uniform.

Next the melted ozokerite from kettle (A) was added to kettle (B). Also added to kettle (B) was the butylated hydroxyanisole (obtained under the tradename TENOX) and the butyl paraben. The ingredients in kettle (B) were mixed well. While maintaining the temperature of kettle (B) at about 80° to about 85° C., the distarch phosphate (obtained from National Starch Co.) was added. The resulting blend is mixed about 15-20 minutes or until uniform.

The titanium dioxide, kaolin, lomicron pink yellow oxide, black oxide and propyl paraben were premixed together using a CBM mixer to form a color mix.

With the resulting mixture in kettle (B) at about 80° C. to about 85° C., the mixer and high shear was started. The high shear was brought to about 900 RPM. The color mix was added slowly to kettle (B) and the RPM were increased as necessary to effect good movement of the batch. The resulting mixture was mixed for about 30-40 minutes.

Then the mixer was stopped to check a sample for undispersed pigment or color spots (an amount of pigment spots will be evident but should not be excessive). If the dispersion is not acceptable the mixture is maintained at about 80°-85° C. and mixing is continued with high RPM for about an additional 25 to 30 minutes. Repeat mixing if necessary.

The temperature should not exceed 95° C.

when the mixture was uniform it was strained through cheese cloth into appropriate containers.

EXAMPLE 2

Following the procedure of Example I, the ingredients in Table II were blended together to produce a composition of this invention.

TABLE II

| Ingredient | % by wt |
| --- | --- |
| White Ozokerite 170 MF | 13.030 |
| SOFTISAN 649 | 5.800 |
| LIPOVOL MOS 70 | 20.110 |
| LIPOVOL MOS 350 | 20.727 |
| Butylated hydroxyanisole (Tenox) | 0.030 |
| Butyl paraben | 0.100 |
| Distarch phosphate | 5.00 |
| Titanium dioxide | 29.236 |
| Kaolin | 4.192 |
| Lomicron Pink | 0.805 |
| Yellow oxide | 0.835 |
| Black oxide | 0.035 |
| Propyl paraben | 0.100 |

Those skilled in the art will appreciate that the total amount of all ingredients (components) used in the compositions of this invention equals 100% by weight of the total composition. Also, unless stated otherwise, all percents herein are percent by weight of the total composition.

The invention being thus described, it will be obvious that the same may be varied in many ways. Such variations are not to be regarded as a departure from the spirit and scope of the invention, and all such modifications are intended to be included within the scope of the claims.

What is claimed is:

1. A cosmetic composition free of mineral oil and free of lanolin comprising:
   (A) an adhesive, softening and stabilizing effective amount in the range of from about 10 to 15% by weight of ozokerite wax;
   (B) a softening, adhesive and skin soothing effective amount in the range of from about 3 to 10% by weight of triglyceride suitable for use in cosmetic compositions, and which is a mixture of the glyceryl esters of caprylic acid, capric acid, isostearic acid and adipic acid;
   (C) an amount of a mixture of esters effective in completely replacing mineral oil while maintaining spreadability of the composition and suitable for use in cosmetic compositions, said mixture comprising:
   (a) about 9 to about 12% by weight of the total composition of tridecyl stearate;
   (b) about 8 to about 11% by weight of the total composition of neopentylglycol dicaprylate/-dicaprate;
   (c) about 9 to about 12% by weight of the total composition of tridecyl trimelitate; and
   (d) about 8 to about 11.5% by weight of the total composition of dipentaerythrityl hexacaprylate/hexacaprate;
   (D) an oil absorbing effective amount in the range of from about 2.5 to 7.5% by weight of distarch phosphate;
   (E) a bulking effective amount in the range of from about 3 to 6% by weight of kaolin;
   (F) a coloring effective amount in the range of from about 28 to 35% by weight of titanium dioxide, yellow oxide, black oxide and lomicron pink; and
   (G) optionally, a preservative effective amount in the range of from about 0.2 to 0.5% by weight of at least one preservative suitable for use in cosmetic compositions.

2. The composition of claim 1 comprising:
   (A) from about 13 to about 14% by weight of ozokerite wax;
   (B) from about 4 to about 5% by weight of said triglyceride;
   (C) from about 36 to about 44% by weight of said mixture of esters;
   (D) from about 4 to about 6% by weight of distarch phosphate;
   (E) from about 3.0 to about 4.5% by weight of kaolin;
   (F) from about 29 to about 32% by weight of said colorants; and
   (G) optionally, from about 0.2 to about 0.3% by weight of said at least one preservative.

3. A cosmetic composition which is free of mineral oil and free of lanolin comprising
   (A) an ozokerite wax in amounts of 13 to about 14% by weight of said composition;
   (B) at least one triglyceride in amounts of about 4 to about 6% by weight of said composition, and wherein said at least one triglyceride comprises a mixture of the glycerol esters of caprylic acid, capric acid, isostearic acid, and adipic acid;
   (C) a mixture of esters suitable for use in cosmetic compositions, said mixture
   (a) a first mixture of esters having a maximum acid value of 0.5 and a saponification value of 268-288; and
   (b) a second mixture of esters having a maximum acid value of 0.5 and a saponification value of 206-226;
   wherein said first and second mixtures of esters (C) comprise:
   (i) about 9 to about 11% by weight of the total composition of tridecyl stearate;
   (ii) about 9 to about 11% by weight of the total composition of neopentylglycol dicaprylate/-dicaprate;
   (iii) about 9 to about 11% by weight of the total composition of tridecyl trimelitate; and
   (iv) about 9 to about 11% by weight of the total composition of dipentaerythrityl hexacaprylate/hexacaprate.
   (D) distarch phosphate present in amounts of about 4 to about 6% by weight of said composition;
   (E) kaolin as a bulking agent present in amounts of about 3 to about 4.5% by weight of said composition;
   (F) at least one colorant selected from the group consisting of:

(i) about 29 to about 30% by weight of said composition of titanium dioxide;
(ii) about 0.8 to about 1.0% by weight of said composition of lomicron pink;
(iii) about 0.8 to about 1.0% by weight of said composition of yellow oxide; and
(iv) about 0.02 to about 0.04% by weight of said composition of black oxide; and (G) optionally, at least one preservative selected from the group consisting of
(i) about 0.025 to about 0.035% by weight of said composition of butylated hydroxyanisole;
(ii) about 0.05 to about 0.15% by weight of said composition of butylparaben; and
(iii) about 0.05 to about 0.15% by weight of said composition of propylparaben.

4. The composition of claim 3 wherein:
(A) said triglyceride is present in amounts of about 5 to about 6% by weight;
(B) said mixture of esters (C) comprises:
(i) about 10 to about 11% by weight of tridecyl stearate;
(ii) about 9 to about 11% by weight of neopentylglycol dicaprylate/dicaprate;
(iii) about 10 to 11% by weight of tridecyl trimellitate; and
(iv) about 9 to 10% by weight of dipentaerythrityl hexacaprylate/hexacaprate;
(C) said distarch phosphate is present in amounts of about 4.5 to about 5.5% by weight; and
(D) said bulking agent is present in amounts of about 3 to about 4% by weight.

5. The composition of claim 3 manufactured in a solid rigid form suitable for use as a cosmetic.

6. The composition of claim 3 manufactured in the form of a cover stick.

* * * * *